(12) United States Patent
Torné Cubiró et al.

(10) Patent No.: US 7,262,057 B2
(45) Date of Patent: Aug. 28, 2007

(54) MAIZE NUCLEOTIDE SEQUENCE CODING FOR A PROTEIN WITH TRANSGLUTAMINASE ACTIVITY AND USE THEREOF

(75) Inventors: José María Torné Cubiró, Barcelona (ES); María Asunción Santos Lozano, Barcelona (ES); David Talavera Baro, Barcelona (ES); Enrique Villalobos Amador, Barcelona (ES); Juan Rigau Lloveras, Barcelona (ES)

(73) Assignee: Consejo Superior de Investigaciones Cientificas, Madrid (ES)

( * ) Notice: Subject to any disclaimer, the term of this patent is extended or adjusted under 35 U.S.C. 154(b) by 0 days.

(21) Appl. No.: 11/000,530

(22) Filed: Nov. 30, 2004
(Under 37 CFR 1.47)

(65) Prior Publication Data

US 2006/0005266 A1    Jan. 5, 2006

Related U.S. Application Data

(63) Continuation of application No. PCT/ES03/00247, filed on May 23, 2003.

(30) Foreign Application Priority Data

May 31, 2002    (ES) .................... 200201253

(51) Int. Cl.
*A01H 5/00*  (2006.01)
*C12N 15/82* (2006.01)
*C12N 15/29* (2006.01)
*C07H 21/00* (2006.01)

(52) U.S. Cl. ............ 435/468; 435/320.1; 536/23.6; 800/278

(58) Field of Classification Search ............ None
See application file for complete search history.

(56) References Cited

U.S. PATENT DOCUMENTS

| | | |
|---|---|---|
| 5,156,956 A | 10/1992 | Motoki et al. |
| 5,726,051 A | 3/1998 | Fraij et al. |
| 5,736,132 A | 4/1998 | Juergensen et al. |
| 5,736,356 A | 4/1998 | Sano et al. |
| 5,928,689 A | 7/1999 | Milkowski et al. |
| 5,948,662 A | 9/1999 | Kobayashi et al. |
| 6,042,851 A | 3/2000 | Matsuura et al. |
| 6,063,408 A | 5/2000 | Yamazaki et al. |
| 6,106,887 A | 8/2000 | Yamazaki et al. |
| 6,190,879 B1 | 2/2001 | Bech et al. |
| 6,270,814 B1 | 8/2001 | Han et al. |
| 6,325,951 B1 | 12/2001 | Soper et al. |
| 6,342,256 B1 | 1/2002 | Oomura et al. |
| 2001/0053398 A1 | 12/2001 | Soeda |
| 2002/0004085 A1 | 1/2002 | Xu et al. |
| 2004/0214272 A1* | 10/2004 | La Rosa et al. ............ 435/69.1 |

FOREIGN PATENT DOCUMENTS

| | | |
|---|---|---|
| EP | 555649 | 8/1993 |
| EP | 0693556 | 1/1996 |
| EP | 0948905 | 10/1999 |
| JP | 2000-354498 | 12/2000 |
| WO | WO97/40701 | 11/1997 |
| WO | WO99/60200 | 11/1999 |
| WO | WO0162888 | 8/2001 |

OTHER PUBLICATIONS

Guo et al. (PNAS, 101: 9205-9210, 2004).*
Villalobos et al. (Gene, 336:93-104, 2004).*
Kira S. Makarova et al, A superfamily of archael, bacterial, and eukaryotic proteins homologous to animal transglutaminases, Proteen Science (1999), 8:1714-1719.
Carlo M. Bergamini et al, Conformational stability of human erthocyte transglutaminase, Eur. J. Biochem. 266. 575-582 (1999).
Lucio Cariello et al, A new transglutaminase-like from the ascidian Ciona intestinalis, FEBS Letters 408 (1997) 171-176.
Donatella Serafini-Fracassini et al, Plant Transglutaminases, Phytochemistry, vol. 40, No. 2, pp. 355-365 (1995).
Laszlo Lorand et al, Transglutaminases, Molecular and Cellular Biochemistry 58, 9-35 (1984).
Fuminori Tokunaga et al, Limulus Hemocyte Transglutaminase, The Journal of Biological Chemistry, vol. 268, No. 1, Issue of Jan. 5, pp. 262-268 (1993).
Akitada Ichinose et al, Structure of Transglutaminases, The Journal of Biological Chemistry, vol. 265, No. 23, pp. 13411-13414 (1990).

(Continued)

*Primary Examiner*—Phuong T Bui
*Assistant Examiner*—Vinod Kumar
(74) *Attorney, Agent, or Firm*—Klauber & Jackson L.L.C.

(57) ABSTRACT

The invention relates to a DNA molecule from maize which codes for a protein with TGase activity and to a gene expression vector comprising said DNA molecule. The invention also relates to the use of the aforementioned DNA molecule or vector in order to produce transformed cells capable of expressing recombinant proteins with TGase activity and to introduce the sequence encoding for a protein with TGase activity into plant cells. In addition, the invention relates to the resulting transgenic plants and cells of microorganisms. Furthermore, the proteins with TGase activity expressed from the above-mentioned DNA sequences can be used, for example, in food manipulation, processing and transformation.

9 Claims, 1 Drawing Sheet

OTHER PUBLICATIONS

Zoltan Nemes et al, Involucrin Cross-linking by Transglutaminase 1, The Journal of Biological Chemistry, vol. 274, No. 16, pp. 11013-11021 (1999).

Isaac Icekson et al, Evidence for Transglutaminase Activity in Plant Tissue, Plant Physiol (1987) 84, 972-974.

Donatella Serafini-Fracassini et al, First Evidence for Polyamine Conjugation Mediated by an Enzymic Activity in Plants, Plant Physiol (1998)87, 757-761.

Stephen A. Margosiak et al, Identification of the Large Subunit of Ribulose 1,5-Bisphosphate Carboxylase/Oxygenase as a Substrate for Transglutaminase in Medicago sativa L. (Alfalfa)[1], Plant Physiol (1990) 92, 88-96.

S. Del Duca et al, Identification of chlorophyll-a/b proteins as substrates of transglutaminase activity in isolated chloroplasts of Helianthus tuberosus L., Planta (1994) 193-283-289.

Stefano Del Duca et al, Factors affecting transglutaminase activity catalysing polyamine conjugation to endogenous substrates in the entire chloroplast, Plant Physiol.Biochem. 2000, 38(6), 429-439.

Dirk Schindelhauer, Construction of mammalian artificial chromosomes: prospects for defining an optimal centromere, BioEssays 21:76-83 (1999).

Esmaragda Bernet et al, Changes in polymaine content, arginine and ornithine decarboxylases and transglutaminase, activites during light/dark phases (of intial differentation) in maize calluses and their chloroplasts, Plant Physiol. Biochem. 1999, 37 (12), 899-909.

E. Villalobos, J.M. Torne et al, Immunogold localization of a transglutaminase related to grana development in different maize cell types, Protoplasma (2001) 216: 155-163.

Patricia Giraldo et al, Size matters: use of YACs, BACs and PACs in transgenic animals, Transgenic Research 10: 83-103, 2001.

Paul D. Robbins et al, Viral vectors for gene therapy, Tibtech Jan. 1998 (vol. 16).

Villalobos E. et al Immunogold Localization of A Transglutaminase Related to Grana Development in Different Maize Cell Types, Protoplasma (2001) vol. 316 (3-4) pp. 155-163.

\* cited by examiner

MAIZE NUCLEOTIDE SEQUENCE CODING FOR A PROTEIN WITH TRANSGLUTAMINASE ACTIVITY AND USE THEREOF

RELATED APPLICATIONS

The present application is a Continuation of co-pending PCT Application No. PCT/ES03/00247 filed May 23, 2003, which in turn, claims priority from Spanish Application Serial No. 200201253, filed on May 31, 2002. Applicants claim the benefits of 35 U.S.C. § 120 as to the PCT application and priority under 35 U.S.C. § 119 as to said Spanish application, and the entire disclosures of both applications are incorporated herein by reference in their entireties.

The invention relates to the identification of new proteins coming from plants with TGase activity and use thereof in the field of food manipulation, processing and transformation and in the development of transgenic plants with new capacities.

PRIOR ART

Transglutaminases (TGase; EC2.3.13) (R-glutaminyl-peptideaminase-γ-glutamyl-transferase) catalyze amide links between a primary amino group of a polyamine or a lysine (amino donor) and a γ-carboxyamide group of a glutamyl of some proteins (amino receptor), by means of an intermediate reaction whereby the enzyme links to the substrate by reaction between the γ-carboxyamide group of the glutamyl residue of the protein and a sufidryl group of a cysteine residue of the active center of the enzyme (Serafini-Fracassini, D., Del Duca, S. & Beninati, S. 1995. Plant Transglutaminases. Phytochemistry 40: 355-365): The result of the TGase activity is: a) modification of the configuration of the protein itself and b) other more extensive changes of configuration as a result of links between the protein itself and between different proteins to form conjugates with a high molecular weight.

There are studies on TGases in humans and also in animals, plants, lower vertebrates, some bacteria, algae and yeast (Makarova, K. S., Aravind, L. & Koovin, E. V. 1999. A superfamily of archaeal, bacterial and eukaryotic proteins homologous to animal transglutaminases Protein Science 8:1714-1719; Bergamini, C. M., Dean, M., Tanfani, F. Ferrari, C. & Scatturin. 1999. Conformational stability of human erythrocyte transglutaminase: Patterns of thermal unfolding at acid and alkaline pH. Eur. J. Biochem. 266: 575-582.; Cariello, L. Ristoratore, F. & Zanitti, L. 1997. A new transglutaminase-like from ascidian Ciona intestinalis. FEBS Lett 408:171-176; Lorand, L. & Conrad. S. M. 1984. Transglutaminases. Mol Cell Biochem 58:9-35; Serafini-Fracassini, D., Del Duca S. & Beninati S. 1995. Plant Transglutaminases. Phytochemistry 40:355-365; Tokunaga, F., Muta, T. Iwanaga, S., Ichinose, A., Davie, EW, Kuma, K. & Miyata, T. 1993. Limulus hemocyte transglutaminase. cDNA cloning, amino acid sequence and tissue localization. J Biol Chem 268:262-268).

The most known TGases are: blood coagulation factor XIII that is a protein of plasma and TGase K implicated in the formation of the stratum corneum epidermidis. On the other hand, some of the genes responsible for some of the cited TGases have already been cloned and the implication of TGases in important processes such as cell differentiation, tissue stabilization or programmed cell death is becoming known (Ichinose, A., Bottenus, R. E. & Davie E. W. 1990. Structure of transglutaminases. J. of Biol. Chemistry. 265 (23): 13411-13414; Bergamini, C. M., Dean, M., Tanfani, F., Ferrari, C. & Scatturin. 1999. Conformational stability of human erythrocyte transglutaminase: patterns of thermal unfolding at acid and alkaline pH. Eur. J. Biochem. 266: 575-582; Nemes, Z., Marekov, L. N. & Steinert, P. M. 1999. Involucrin cross-linking by transglutaminase 1. J. of Biol. Chemistry. 274(16): 11013-11021). These enzymes also seem to be implicated in neurodegenerative diseases, tumors, celiac diseases, etc., and therefore, they are a group of very interesting enzymes in clinical studies. Regarding these clinical studies there are different patents related to TGases: U.S. Pat. No. 5,736,132 "Method of promoting adhesion between tissue surfaces" filed by Orthogene, Inc., 1998; U.S. Pat. No. 5,726,051 "Transglutaminase gene" filed by Oklahoma Medical Research Foundation, 1998.

The function of plant TGases is less known although the first data about the existence thereof were published some years ago (Icekson I. & Apelbaun, A. 1987. Evidences for transglutaminase activity in plant tissue. Plant Physiol. 84. 972-974; Serafini-Fracassini D., Del Duca S., & D'Orazi D. 1988. First evidence for polyamine conjugation mediate by an enzyme activity in plants. Plant Physiol. 87:757): Studies on plants have been centered above all on biochemical aspects related to the activity, substrates on which same acts and tissues where it is abundant, but its functional role wherein partial data about its intervention, such as: growth and development, morphogenesis in general, photosynthesis and cell death, has not been studied (Margosiak, S. A., Drama, A., Bruce-Carver, M. R., Gonzalez, A. P. Louie, D. & Kuehn. 1990. Identification of the large subunit of ribulose 1,5-biphosphate carboxylase/oxygenase as a substrate for transglutaminase in Medicago sativa L. (Alfafa): Plant Physiol. 92: 88-96; Del Ducca, S., Tidu, V., Bassi, R. Exposito, C., & Serafini-Fracassini, D. 1994, Identification of chlorophyll-a/b proteins as substrates of transglutaminase activity in isolated chloroplasts of Helianthus tuberosus L. Planta 193:283-289; Del Ducca, S., Della Mea, M., Munoz de Rueda, P. & Serafini-Fracassini, D. 2000 Factors affecting transglutaminase activity catalyzing polyamine conjugation to endogenous substrates in the entire chloroplast. Plant Physiol Biochem 38:429-439).

Besides, it is to be emphasized that transglutaminase has an added value for biotechnological purposes. This new supplementary facet as an interesting metabolite comes from its capacity to create covalent links between different proteins. This property has been used, for example, to keep the texture of goods such as fish and meat, reducing the need to use salts (surimi, etc.). For the formulation of gelatins with a different density, etc. For preparing precooked foods with less fat (tofu). It is also possible to keep the consistency, elasticity, moisture or viscosity of a product at different temperatures. Likewise, it is used in different dairy processed foods: cheeses, yogurts, ice creams, etc. So much so, that it is currently used as an "additive" in many bio processed foods, the recommended doses is 65 ppm for this purpose in the USA.

All these possibilities of TGase have produced the creation of different patents on: methods for obtainment, use, etc. and they have made this substance a commercial product such as, for example, those that the firm Ajinomoto has been distributing with the name: Activa TG.RTM. The companies that market the product are Ajinomoto Co., Inc. of Tokyo (widespread also in the U.S.) and Rohm Enzyme of USA. However, in Spain no firm that is dedicated to the industrial production of TGase has been found in Spain.

The first TGase that has been overexpressed for commercial purposes such as the above-cited ones, was carried out with bacteria (*Streptoverticillium* sp.) by the firm Ajinomoto, which patented the process and the subsequent different improvements of this initial protocol (U.S. Pat. No. 5,156,956 "Transglutaminase" (1992)). Likewise, this same firm has patented, another similar system, but by means of transformation of *Crassostrea gigas* (U.S. Pat. No. 5,736,356 "Transglutaminase originating from *Crassostrea gigas* (1998)) and from *Bacillus subtilus* (U.S. Pat. No. 5,948,662 "*Bacillus*-derived transglutaminase" (1999)).

Over the last few years, the research group, which is the inventor of the present invention, has, likewise, done previous studies on a biochemical level. About the implication of TGase on the morphogenesis of maize calluses and their relationship with light (Bernet, E., Claparols, I., Dondini, L., Santos, M. A., Serafini-Fracassini, D. & Torné, J. M$^a$. 1999. Changes in polyamine content, arginine and ornithine decarboxylases and transglutaminase activities during light/dark phases (of initial differentiation) in maize calluses and their chloroplast. Plant Physio Biochem. 37(12): 899-909): Besides, immunolocalization of this enzyme in different corn cell systems, in relation to the development of chloroplasts has been recently published (Villalobos, E. Torné, J. M., Ollés, C., Claparols, I. & Santos, M. A. 2001, Subcellular localization of a transglutaminase related to grana development in different maize cell types. Protoplasma. 216: 155-163). However, no results on the molecular identification and functional activity with plant transglutaminases have been found, therefore, new knowledge about said transglutaminases is of utmost commercial interest.

DESCRIPTION OF THE INVENTION

Brief Description

The invention faces the problem related to the scarcity of TGase coming from plants needed in the field of food manipulation and transformation and in the development of transgenic plants with new capacities.

The solution provided by this invention is based on the fact that the inventors have identified some DNA sequences with TGase activity. (TGase; EC2.3.2.13) from corn. The TGase activity of proteins encoded from said DNA sequences has become evident in experiments with extracts of these proteins.

Therefore, an object of this invention is said DNA molecules.

Another additional object of this invention is a vector that comprises, at feast, one of said DNA molecules.

Another additional object of this invention comprises the use of said DNA molecules or of said vectors to produce transformed cells capable of expressing recombinant proteins with TGase activity, or to introduce said encoding sequence of a protein with TGase activity into plant cells. The cells of microorganisms and the resulting transgenic plants also comprise additional objects of this invention.

Another additional object of the present invention constitutes the proteins with TGase activity expressed from said DNA sequences and use thereof in food manipulation and transformation.

DETAILED DESCRIPTION OF THE INVENTION

The invention provides a DNA molecule, hereinafter DNA molecule of the invention, coming from plants and encoding a protein with TGase activity that comprises a nucleotide sequence selected from among:

a) the nucleotide sequence identified as SEQ ID NO 1, SEQ ID NO3 or a fragment thereof; and
b) a nucleotide sequence similar to the sequence defined in a).

In the sense used in this description, the term "similar" is meant to include any DNA sequence that can be isolated or made on the basis of the nucleotide sequence shown in SEQ ID NO 1 or SEQ ID NO 3, for example, by means of introducing conservative or non-conservative nucleotide substitutions, including the insertion of one or more nucleotides, adding one or more nucleotides in any of the ends of the molecule or deletion of one or more nucleotides in any end or inside the sequence.

In general, a similar DNA molecule is substantially homologous to the nucleotide sequence identified as SEQ ID NO 1 or SEQ ID NO 3. In the sense used in this description, the expression "substantially homologous" means that the nucleotide sequences in question have a degree of identity, at the nucleotide level, of, at least 60%, preferably of, at least 85%, or more preferably of, at least 95%.

The DNA molecule of the invention comes from corn and can be found in similar forms in other species of higher plants, among others, rice, wheat, *Arabidopsis*, etc., where they may be in a natural form or in another case, they could also be the result of a genic transformation process wherein the transformed organism reproduces said DNA molecules. The DNA molecule of the invention may be isolated, by means of conventional techniques, from the DNA of any plant that contains it, by means of use of probes or oligonucleotides, prepared thanks to the information of the nucleotide sequence of said DNA molecule, provided in this invention.

The DNA molecule of this invention includes fragments thereof that have said TGase activity.

In a particular embodiment, the DNA molecule of the invention is a DNA molecule of corn of SEQ ID NO1 or of SEQ ID NO 3.

The DNA molecule of the invention may be used, in general, in the generation of an expression vector, hereinafter expression vector of the invention that permits expression of these proteins with TGase activity in a wide range of host cells. In general, the expression vector of the present invention comprises, at least, one DNA sequence of the invention and, at least, a promoter that directs transcription of the gene of interest, to which it is operatively bonded, and other sequences necessary or appropriate for the transcription of the gene of interest and its suitable adjustment in time and place, for example, signs of beginning and termination, cutting sites, sign of polyadenylation, source of replication, transcriptional enhancers, transcriptional silencers, etc. Examples of suitable expression vectors may be selected in accordance with the conditions and needs of each specific case among plasmides, yeast artificial chromosomes (YACs), bacteria artificial chromosomes (BACs), artificial chromosomes based on P1 bacteriophage (PACs), cosmides or viruses, that may also contain, a bacterial source or yeast replication source so that it may be amplified in bacteria or yeasts, as well as a marker usable to select transfected cells other than the gene or genes of interest. Therefore, the invention also refers to a vector that comprises a DNA molecule of the invention. The selection of the vector will depend on the host cell wherein the vector is later going to be introduced. For example, the vector where said DNA sequence is introduced may be a plasmide that, when it is introduced into a host cell, it integrates into the genome of said cell and is replicated together with the chromosome of the host cell.

The vector of the invention may be obtained by conventional methods known by experts in the field (Kovesdi et al.—1997. Curr Opin Biotech 8:583-589 Transgenic Res. 10:83-103; Coffin et al. 1998. Retroviruses, CSHLP; Robbins et al. 1998. Trends Biotech. 16:35-40; Anderson. 1998. Nature 392:25-30; Schindelhauer. 1999. BioEssays 21:76-83): A particular object of the present invention comprises the plasmides pGEMT15 and pGEMT21 that contain the SEQ ID NO 1 and SEQ ID NO 3, respectively.

The invention also provides a cell that comprises a DNA molecule or expression vector of the invention. The host cells that can be transformed with said expression vector may be, for example, GRAS bacterial cells and yeasts. The cells that contain the expression vector of the present invention may be used for overproduction of proteins with TGase activity encoded by the DNA molecule of the present invention. A particular object of the present invention is comprised of a protein with TGase activity, among others, with an amino acid sequence as described in SEQ ID NO 2 and SEQ ID NO 4.

These results permit the creation of new possibilities to transform a GRAS (Generally Recognized as Safe) bacterial system or a yeast that would be useful, by means of the heterologous expression, to produce the cited new TGase proteins. As it has been indicated above, a protein with TGase activity may be used in multiple food manipulation, processing and transformation processes thanks to its capacity to create covalent links between different proteins. This characteristic has been used, for example, to keep the texture of foods such as fish and meat, reducing the need to use salts, see patent U.S. Pat. No. 5,928,689 "Method for treating PSE meat with transglutaminase", WO 0162888 "Improved composition of marine product"; for producing gelatins with a different density; for preparing precooked foods with less fat (tofu), see U.S. Pat. No. 6,342,256 "Tofu products excellent in freeze resistance and process for producing the same", U.S. Pat. No. 6,042,851 "Process for producing packed tofu". It is also possible to keep the consistency, elasticity, moisture or viscosity of a product at different temperatures. Likewise, it is used in different dairy processed foods: cheeses (U.S. Pat. No. 6,270,814 "Incorporation of whey into process cheese", application US 20010053398 "Cheese whey protein having improved texture process for producing the same and use thereof"), yogurts, ice cream, mayonnaise, sauces and in producing noodles (EP 0948905 "Enzyme preparations comprising transglutaminase and process for producing noodles", U.S. Pat. No. 6,106,887 "Process for obtaining a modified cereal flour), for chocolate (U.S. Pat. No. 6,063,408 "Process for producing chocolate"), for products derived from potatoes (US application 20020004085 "Methods for producing potato products"), of sugar (JP 200354498 "Production of sugar from cereal flour material by transglutaminase treatment"). The different uses, among others, described in the preceding patents for TGases are examples of the potential uses of the TGases of the present invention. Therefore, a particular object of the present invention is the use of proteins with TGase activity of the present invention, among others, the proteins SEQ ID NO 2 and SEQ ID NO 4, or solutions that contain them, in food manipulation, processing and transformation. Hereinafter the review of Chiya Kuraishi et al., 2001 (Transglutaminase: Its utilization in the food industry Food Reviews International 17 (2):221-246), is indicated as an example of the uses of the proteins with TGase activity of the present invention.

Finally, there are other uses different from the ones commented on above of proteins with TGase activity of the present invention and of those that are indicated as an illustration of said uses, there are the following patents, among others: "Method for enzymatic treatment of wool" U.S. patent application Ser. No. 161824 (1998) MacDevitt et al., April 2000; "Enzymatically protein encapsulating oil particles by complex coacervation application no. 791953 (1997). Soper, Jon C. et al. March 2000; "Cross-linked gelatin gels and method of making them" application No. 641463 (1996) Bishop, P. D. et al. ZymoGenetics, Inc. (Seattle, EA, USA); Process for obtaining a modified cereal flour" application no. 977575 Ajinomoto Co. Inc. (Tokyo, Japan). Yamazaki et al. August 2000; "Microbial transglutaminase, their production and use" application no. 294565 (1999). NovoNordisk A/S (Bagsvaerd, D K) Bech et al. February 2001.

Besides, the DNA molecule or expression vector of the invention may be used in genetic transformation processes of plants for basic research as well as for the development of transgenic plants with new capacities produced by the manipulation of functions attributed to said TGase (plant growth and development, morphogenesis, photosynthesis and cell death) by means of altering the expression of said proteins.

Figure 1:
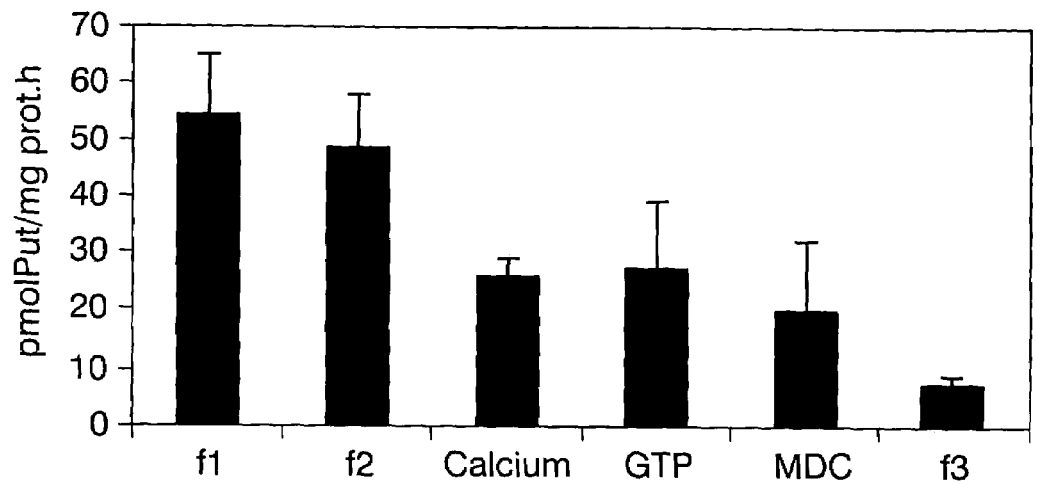
FIG. 1. TGase activity (measured in pmol of Put Incorporated) of a protein extract corresponding to each one of the products of phagous lysis described in the part about methodology, corresponding to positive phages f1 and f2 (that contain a different cDNA of corn TGase: f1=SEQ ID NO1 and f2=SEQ ID NO 3) and to the negative phage f3 (that does not contain any cDNA of TGase). Besides, the effect of different factors that influence the TGase activity of the extracts, described as inherent of said enzymatic TGase activity in other systems is shown: Calcium=the protein extract and in the absence of calcium. GTP=addition of 1 mM of GTP. MDC=addition of 1 mM of MDC.

a=40 mg protein/ml. b=60 mg protein/ml. c=80 mg protein/ml.

EXAMPLES OF THE INVENTION

Example 1

Isolating and Cloning Two cDNAS Coding for Two Proteins of the Family of Corn Transglutaminases by Means of Immunoscreening Expression Bank The cDNAs of the present invention were isolated from a cDNA expression bank, in Lambda-ZAPII®, made from EcoRI and XhoI targets, starting with a RNA messenger of two-week old *Zea mays* subsp. *mays* plantulae, growing homozygote B73, growing under greenhouse conditions (donated by Dr. Alice Barkan, of the University of Oregon, USA).

A plant transglutaminase of 58 kDa purified with extracts of chloroplasts of *Helianthus* tuberosus leaves was used as an antigen. A polyclonal antibody was obtained in a hen (Villalobos, E., Torné, J. M., Ollés, C., Claparols, I. & Santos, M. A. 2001. Subcellular localization of a transglutaminase related to grana development in different maize cell types. Protoplasma. 216:155-163). The specificity of the antibody was determined by the dot blot technique, using commercial pig liver transglutaminase, as well as by western blot with purified protein (Dondini, L. 1998. "Poliammine legate e transglutaminasi nelle plante." PhD. Thesis. University of Bologna, Italy). Titration was carried out by the western blot technique. (The complete methodology is specified in detail in our study: Villalobos, E., Torné, J. M., Ollés, C.-, Claparols, I. & Santos, M. A. 2001. Subcellular localization of a transglutaminase related to grana development in different maize cell types. Protoplasma. 216:155-163).

Immunoscreening of the Bank

Once the title of the bank used is known, a colony of the XL-Blue® strain is inoculated into a liquid LB medium containing $MgSO_4$ and 20% maltose.

After growing the bacteria until a DO of 2.0 (600 nm) is attained, the mixture of the bacterial culture is made with $4.5 \times 10^4$ pfu from the library, to which 10 mM of IPTG is added. After infecting and inoculating Petri dishes with the LB culture medium+10 mM $MgSO_4$, a disk of nitrocellulose saturated with 10 mM of IPTG is placed over them. After incubating the Petri dishes with the filter for 4 hours, they are cooled and the filter is washed with PBS. Finally, once the membrane is blocked with skim milk or BSA, it is developed and marked with an antibody. In order to detect lysis where the positive phages that have interacted with the antibody against *H. tuberosus* transglutaminase are found, western blot analysis is done of said membrane and it is developed on a photographic plate by means of the ECL reagent.

Excision In Vivo of Phagemides in pBluescript SK– and Selection of Positive Colonies Once the two phages that contain the cDNAs that respectively code for a protein that interacts with the antibody have been isolated and purified, then they are excised by the "ExAssist™ Interference-Resistant Helper Phage (Stratagene)". Coinfecting is done in XL1-Blue strains and infecting is done in XLOLR®. Dishing is done in a selective medium that determines the vector used (pBluescript). In our case, the culture medium that selects transforming colonies is LB-agar added with ampicillin (50 µg/ml), 1 mM IPTG and the X-Gal substrate (40 µg/ml), of the enzyme β-galactosidase, whose gene is interrupted by the insert or cDNA.

Small Scale Isolation of Plasmides (MINIPREP).

For each excision, isolation of the plasmid DNA, that contains the cDNA of interest, is carried out by a small scale MINIPREP technique of the bacterial lysis using SDS and NaOH, neutralized with potassium acetate and purified with a mixture of phenol:chloroform:isoamyl-alcohol (25:24:1) and precipitating with ethanol. Then it is resuspended with TE 1× Buffer added with the RNAase enzyme.

Checking the Presence of cDNA in the pBluescript Vector

In each case, the checking of the presence of the insert in pBluescript is done by digesting a sample of the plasmide DNA, obtained with the same endonuclease enzymes with which the bank (EcoRI and XhoI) was made. Digesting is done according to the requirements of each restriction enzyme (Buffer and temperature). Once digesting has been carried out, the cDNA or insert is released from the vector. This is checked with conventional electrophoresis in 0.5% agarose gel in TBE 1× or TAE 1× Buffer.

Sequentiation (Sequentiation Service of IBMB, "CSIC" of Barcelona).

Once the samples of the minipreparations that contain the cDNAs of interest, have been identified, that turned out to be two in our case, they are precipitated and purified by using the mixture of phenol, chloroform and isoamyl alcohol and pure chloroform before the sequentiation process. The samples to be sequenced were dissolved in water.

Determination of the Complete Encoding Sequence by the RACE Technique

The excisions of the two phages in pBluescript SK– made it possible to obtain two partial cDNAs whose complete encoding sequence was defined by means of the RACE technique. For this purpose, from the total RNA removed from the corn leaf, messenger RNA purified by a polydT column, which is used as a mold for the synthesis of simple chain DNA, is obtained. In order to do so, a specific oligonucleotide deduced from the known cDNA sequence (oligo E1,3'-5':GATTCTCCCTGATAAG, SEQ ID NO 5) and reverse transcriptase enzyme. After adding a polyT tail to the simple chain DNA by means of terminal deoxytransferase enzyme (TdT), then the second DNA chain is obtained. This is done by the PCR technique using the oligonucleotide 5' RACE Abridged Anchor Primer (GIBCO BRL®), specific for DNA with a polyT tail (oligo ANCHOR 5'-3':GGCCAGGCGTCGACTAGTACGGGI-IGGGIIGGGIIG, SEQ ID NO 6) and a second specific oligonucleotide of the partial cDNA with a known sequence, specified above, and that corresponds to the oligo E2,3'-5': GTTCTCCAGCATCTCCAG, SEQ ID NO 7).

With the subsequent PCR cycles, said DNA is broadened. The sequence of the cycles was the following: first 2 minutes at 94° C. and then 34 cycles of: 30 seconds at 94° C. for oligo no. 1, but 30 seconds at 60° C. for oligo no. 2, followed in both cases by 7 seconds at 72° C. Finally, it is left at 5° C. for a few hours.

The PCR product is cloned in a suitable vector (such as pGEMT), using lygase enzyme. Then, *E. coli* strains of the DH5-alpha type are transformed and bacteria are grown in a selective culture medium. The plasmide DNA is removed by the above-described Miniprep technique, purified and the obtained fragment is sequenced. In our case, for both partial cDNA sequences, the fragment needed to complete the encoding sequence, proved to be of only four nucleotides. The complete nucleotide encoding sequences, including the four nucleotides obtained by the RACE technique, are described in SEQ ID NO 1 and SEQ ID NO 3, respectively. The expression vectors containing the sequences SEQ ID NO 1 and SEQ ID NO 3 and used for transforming the host cells are the plasmide pGEMT15 and pGEMT21, respectively.

The amino acid sequences obtained from the nucleotide sequences have homologies with the domains of the transglutaminase type active center of other described non-plant systems, in the area corresponding to the amino acids: 431-474 for the protein of SEQ ID NO 2 (60.97 kDa) and 485-528 for the protein of SEQ ID NO 4 (67 kDa). In both cases, a cysteine (Cys) described as an essential amino acid for the activity of the enzyme (Cys439 in SEQ ID NO 2 and Cys493 in SEQ ID NO 4) is found in these areas. Besides, as indicated in sequences SEQ ID NO 1 and SEQ ID NO 3, some regions of 27 nucleotides repeated in tandem in both sequences, SEQ ID NO 1 and SEQ ID NO 3, are observed, although in a different amount, from 15 to 21 repetitions, respectively and with small variations of the nucleotides among some of them. It should be emphasized that these cited repeated regions have not been described before in known TGases. Therefore, they are characteristic of the DNA molecule of the present invention.

Example 2

Checking the Transglutaminase Activity of the Proteins Expressed by said cDNAs

Determination of the TGase Activity of the Protein Expressed by the cDNA

With each one of the two clones of the phages containing the cDNAs of interest, an *E. coli* (XL-Blue strain) culture is infected in a liquid LB culture medium, to which 10 mM IPTG are added. After lysis at 37° C., the concentration of the total protein of the extract is quantified by the Lowry method (Lowry O H, Rosebrough N J, Farr, A L & Randall R J. 1951. Protein measurement with the Folin phenol reagent. J. Biol. Chem. 193:265-275) and with it the tests described hereinafter are carried out, in order to determine the transglutaminase activity in contrast to a lysis extract with a phage that does not contain the cDNA of interest.

Method for Detecting TGase Activity by Determining the Proteins Marked with Tritiated Putrescine An enzyme extract is prepared with each one of the lysis extracts obtained with both phages (f1 that contains TGase of SEQ ID NO 2 and f2 that contains TGase of SEQ ID NO 4), in a concentration of total proteins of 600 μg, and an enzyme test is carried out at 30° C. for 30 minutes. The enzyme mixture contains, aside from the protein extract, 0.6 mM of putrescine, 185 kBq of tritiated putrescine (0.85 TBq/nmol), 20 mM of Tris-HCl* pH 8 and 3 mM of $CaCl_2$. The reaction is blocked with 10% trichloroacetic acid containing 2 mM of putrescine. The samples are repeatedly precipitated and the radioactivity of the pellet is measured (Bernet, E., Claparols, L., Dondini, L., Santos, M. A., Serafini-Fracassini, D.- & Torné, J. $M^a$ 1999): Changes in polyamine conten t, arginine and ornithine decarboxylases and transglutaminase activities during light/dark phases (of initial differentiation) in maize calluses and their chloroplast. Plant Physio Biochem. 37(12): 899-909). The TGase activity is measured in pmols of putrescine per milligram of protein per hour and it was greater in the protein extracts obtained from phages f1 and f2 with respect to the extract from a phage that does not contain any cDNAs of these TGase.

2. Method for Detecting TGase Activity by Means of an Elisa Type Test, Using CBZ-Gln-Gly as the First Substrate and Biotincadaverine as the Second Substrate.

This test consists of a kit provided by the firm Covalab®, which determines, from small amounts of total protein, the TGase activity of the sample, with respect to a commercial TGase of pig liver. The method detects the glutamyl derivatives formed from the peptide and from the polyamine substrate, by TGase activity of the sample by means of a colorimetric test. The activity is measured in TGase units, considering that 0.6 mU of commercial TGase corresponds to an absorbency at 450 nm 1±0.05 OD.

The two protein extracts corresponding to the two lysis products show TGase type activity in the two methods for detecting said activity used and described above (f1 and f2) in comparison with the extract coming from a phage that does not contain any of these cDNAs. The data are shown in FIGS. 1 and 2.

Figure 2:
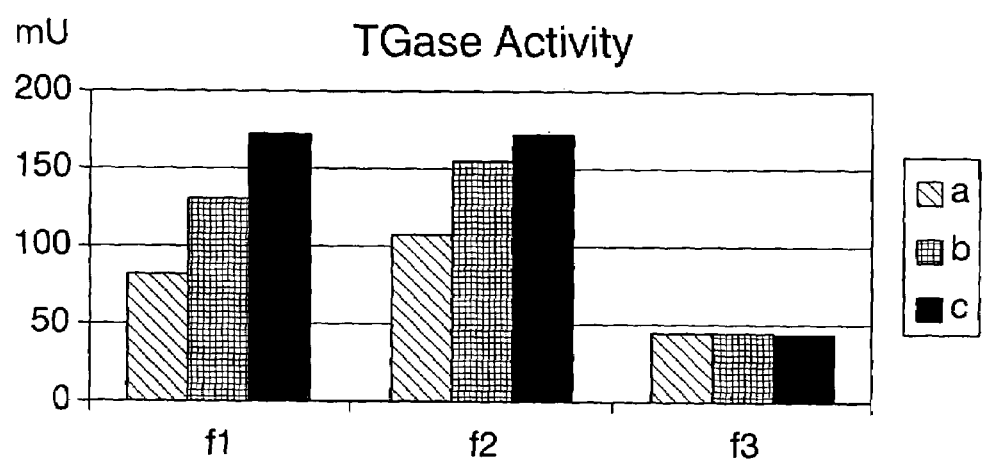
FIG. 2. Activity of the two protein extracts corresponding to the two independent phages that contain the two cDNA of TGase (f1=SEQ ID NO 1; f2=SEQ ID NO 2), with respect to a phage that does not contain any of these cDNA ([3), with respect to the amount of protein of the test. The activity is measured in milliunits (mU) of TGase, by including biotincadaverine, as described in the part of methodology.

Besides, FIG. 1 shows the effect of different factors on the TGase activity of the extracts, described as inherent to said TGase enzyme activity. Hence, the activity of the expressed protein significant reduces: a] in the absence of calcium, b] in the presence of 1 mM of GTP, c] in the presence of 1 mM of denodansylcadaverine (MDC) and d] in the lysis extract with a phage that does not have the cDNA of interest (f3).

A pair of cultures of the bacteria derived from *Escherichia coli*, dH5α type, transformed with a plasmide (pBlueScript) that contains a corn cDNA and carriers of a plasmide that contains the gene encoding the protein of sequence SEQ ID NO 2 and SEQ ID NO 4 of corn, respectively, identified as 15TGZMO2 and 21TGZM02, have been deposited in the Spanish Culture Type Collection ("Colección Española de Cultivos Tipo (CECT")), University of Valencia, Research Building, Burjasot Campus, 46100 Burjasot, Valencia, Spain, 7 (?) May 2002. The "CECT" deposit number corresponds to them: 5705 for 15TGZM02 and 5706 for 21TGZM02, respectively.

The invention claimed is:

1. An isolated nucleotide sequence of SEO ID NO: 1 isolated from corn encoding a protein with TGase (transglutaminase) activity.

2. An expression vector containing the nucleotide sequence according to claim 1.

3. The expression vector according to claim 2 wherein said expression vector is plasmid pGEMT15 having deposit number CECT 5705.

4. A transformed cell comprising the expression vector according to claim 2 and wherein the transformed cell expresses the protein with TGase activity.

5. A process for the production of a recombinant protein with TGase activity, comprising transforming a cell with an expression vector, wherein the expression vector comprises the nucleotide sequence according to claim 1, and wherein said transformed cell expresses the recombinant protein.

6. A method for producing a transgenic plant comprising transforming a plant cell with the expression vector according to claim 2 and regenerating the transgenic plant from the transformed plant cell.

7. A process for the production of the recombinant protein with TGase activity according to claim 5, wherein said protein comprises the amino acid sequence of SEQ ID NO 2.

8. A method for producing a transgenic plant comprising transforming a plant cell with the expression vector according to claim 3 and regenerating the transgenic plant from the transformed plant cell.

9. A transformed cell according to claim 4 wherein said transformed cell is *E. coli* strain having deposit number CECT 5705.

* * * * *

SEQUENCE LISTING

```
<160> NUMBER OF SEQ ID NOS: 7

<210> SEQ ID NO 1
<211> LENGTH: 1748
<212> TYPE: DNA
<213> ORGANISM: Zea mays L
<220> FEATURE:
<221> NAME/KEY: repeat_region
<222> LOCATION: (823)..(1228)
<223> OTHER INFORMATION: rpt unit (823).. (849) number rpt: 15 repeats
<220> FEATURE:
<221> NAME/KEY: 3'UTR
<222> LOCATION: (1606)..(1729)
<223> OTHER INFORMATION: 3'untranslated region
<220> FEATURE:
<221> NAME/KEY: polyA_site
<222> LOCATION: (1730)..(1748)
<223> OTHER INFORMATION: polyadenylation site
<220> FEATURE:
<221> NAME/KEY: CDS
<222> LOCATION: (1)..(1605)
```

<223> OTHER INFORMATION: coding sequence
<300> PUBLICATION INFORMATION:
<308> DATABASE ACCESSION NUMBER: AJ421525
<309> DATABASE ENTRY DATE: 2001-12-06 confidential until 2002-12-06

<400> SEQUENCE: 1

```
atg gct cat cgt gga cat cta gat gga ctg act ggc caa gct cct gct      48
Met Ala His Arg Gly His Leu Asp Gly Leu Thr Gly Gln Ala Pro Ala
 1               5                  10                  15 ctt atg cgc cat ggt tcc ttc gct gca ggc agc ctc tct agc cgc tca      96
Leu Met Arg His Gly Ser Phe Ala Ala Gly Ser Leu Ser Ser Arg Ser
             20                  25                  30 cct ttg cag tct tca tcc aca ctg gag atg ctg gag aac aag ctt gcc     144
Pro Leu Gln Ser Ser Ser Thr Leu Glu Met Leu Glu Asn Lys Leu Ala
         35                  40                  45 atg caa act aca gaa gtg gaa aag ctt atc acg gag aat cag cgg tta     192
Met Gln Thr Thr Glu Val Glu Lys Leu Ile Thr Glu Asn Gln Arg Leu
     50                  55                  60 gca tca agc cat gtg gtc ttg agg cag gac att gtt gat acg gag aaa     240
Ala Ser Ser His Val Val Leu Arg Gln Asp Ile Val Asp Thr Glu Lys
 65                  70                  75                  80 gag atg caa atg atc cgc acc cac cta ggt gaa gtt cag aca gag act     288
Glu Met Gln Met Ile Arg Thr His Leu Gly Glu Val Gln Thr Glu Thr
                 85                  90                  95 gat ttg cag att aga gat ttg ttg gag aga atc aga tta atg gag gta     336
Asp Leu Gln Ile Arg Asp Leu Leu Glu Arg Ile Arg Leu Met Glu Val
            100                 105                 110 gat ata cat agt ggt aat gta gtg aac aag gag ctt cac caa atg cat     384
Asp Ile His Ser Gly Asn Val Val Asn Lys Glu Leu His Gln Met His
        115                 120                 125 atg gag gca aag aga ctt att act gaa agg cag atg cta acc ctt gag     432
Met Glu Ala Lys Arg Leu Ile Thr Glu Arg Gln Met Leu Thr Leu Glu
    130                 135                 140 ata gag gat gtg act aaa gaa tta cag aaa ctc tct gcc tct ggg gac     480
Ile Glu Asp Val Thr Lys Glu Leu Gln Lys Leu Ser Ala Ser Gly Asp
145                 150                 155                 160 aat aaa agc ctt cct gaa ttg ctt tct gag cta gat agg cta cgg aaa     528
Asn Lys Ser Leu Pro Glu Leu Leu Ser Glu Leu Asp Arg Leu Arg Lys
                165                 170                 175 gag cat cat aat tta cga tct cag ttt gaa ttt gag aaa aat aca aac     576
Glu His His Asn Leu Arg Ser Gln Phe Glu Phe Glu Lys Asn Thr Asn
            180                 185                 190 gtc aag caa gtt gag cag atg cgg aca atg gaa atg aac ttg ata acc     624
Val Lys Gln Val Glu Gln Met Arg Thr Met Glu Met Asn Leu Ile Thr
        195                 200                 205 atg acc aaa caa gct gag aag tta cgt gtt gat gtg gca aat gct gaa     672
Met Thr Lys Gln Ala Glu Lys Leu Arg Val Asp Val Ala Asn Ala Glu
    210                 215                 220 aga cgg gca caa gca gct gcg gct caa gca gca gca cat gca gct ggt     720
Arg Arg Ala Gln Ala Ala Ala Ala Gln Ala Ala Ala His Ala Ala Gly
225                 230                 235                 240 gca cag gtg aca gct tcg cag cct gga cag ctc aag cta cca cgg ttt     768
Ala Gln Val Thr Ala Ser Gln Pro Gly Gln Leu Lys Leu Pro Arg Phe
                245                 250                 255 cag cag cag cag cca cag act cat atg cag gtg cat ata cca gct acc     816
Gln Gln Gln Gln Pro Gln Thr His Met Gln Val His Ile Pro Ala Thr
            260                 265                 270 ccc ctg cat atc agc agg gag ccc agg ctg ggg cat atc agc agg gtg     864
Pro Leu His Ile Ser Arg Glu Pro Arg Leu Gly His Ile Ser Arg Val
        275                 280                 285
```

-continued

```
ctc agg ctg ggg tat atc agc agg gag ccc agg ctg ggg cat atc agc      912
Leu Arg Leu Gly Tyr Ile Ser Arg Glu Pro Arg Leu Gly His Ile Ser
    290             295                 300 agg gag ccc agg ctg ggg cat atc agc agg ggg gcc agg atg ggg cat      960
Arg Glu Pro Arg Leu Gly His Ile Ser Arg Gly Ala Arg Met Gly His
305                 310                 315                 320 atc agc agg ggg ctc agg ctg ggg cat atc agc agg gag ccc agg ctg     1008
Ile Ser Arg Gly Leu Arg Leu Gly His Ile Ser Arg Glu Pro Arg Leu
            325                 330                 335 ggg cat atc agc agg gag ccc agg ctg ggg cat atc agc agg gtg ctc     1056
Gly His Ile Ser Arg Glu Pro Arg Leu Gly His Ile Ser Arg Val Leu
        340                 345                 350 agg ctg ggg cat atc agc agg gag ccc agg ctg ggg cat atc agc agg     1104
Arg Leu Gly His Ile Ser Arg Glu Pro Arg Leu Gly His Ile Ser Arg
    355                 360                 365 ggg ccc agt ctg ggg cat atc agc agg ggg ccc agg ctg ggg cat atc     1152
Gly Pro Ser Leu Gly His Ile Ser Arg Gly Pro Arg Leu Gly His Ile
370                 375                 380 agc agg gag ccc agg atg ggg cat atc agc agg gag ccc agg atg ggg     1200
Ser Arg Glu Pro Arg Met Gly His Ile Ser Arg Glu Pro Arg Met Gly
385                 390                 395                 400 cat atc agc agg gtg ctc agg ctg gag cat aca act atg ctt atg atg     1248
His Ile Ser Arg Val Leu Arg Leu Glu His Thr Thr Met Leu Met Met
            405                 410                 415 ctg gca cgg ctt atg cat atg cag gtt act ctg gct atc cag ttg cag     1296
Leu Ala Arg Leu Met His Met Gln Val Thr Leu Ala Ile Gln Leu Gln
        420                 425                 430 gct acg cgc aaa gtg cag tgc cca act att cct atg ctg cac ctc cgc     1344
Ala Thr Arg Lys Val Gln Cys Pro Thr Ile Pro Met Leu His Leu Arg
    435                 440                 445 agc caa caa gca gcg gtg cag cta cga acg ccg cag gag gcc agt atg     1392
Ser Gln Gln Ala Ala Val Gln Leu Arg Thr Pro Gln Glu Ala Ser Met
450                 455                 460 ggg cag ttg gta gtg ctg gat atc cta ctg ggc aag ttc agc cga gca     1440
Gly Gln Leu Val Val Leu Asp Ile Leu Leu Gly Lys Phe Ser Arg Ala
465                 470                 475                 480 gtg gca ctg caa atg cag cgc aag cac ctc ctc ctc cac cac cac cgg     1488
Val Ala Leu Gln Met Gln Arg Lys His Leu Leu Leu His His His Arg
            485                 490                 495 cag cac cat atc ccc cca gca cat atg acc aaa cca gag gag ccc aga     1536
Gln His His Ile Pro Pro Ala His Met Thr Lys Pro Glu Glu Pro Arg
        500                 505                 510 gat aaa atc tgg gat gta aac cag atg gat gtt tgc cat gca cat ttg     1584
Asp Lys Ile Trp Asp Val Asn Gln Met Asp Val Cys His Ala His Leu
    515                 520                 525 ttg agc aga caa ata tgg tga aatctgggat gtaaaccag atggctgtct         1635
Leu Ser Arg Gln Ile Trp
530 gtgcctccat cccattgact agggcgtatt ttcaccaata ttgtgcctcc agtgcaattt   1695 cttctgtgtt atatatcacc accatttgtt gagcaaaaaa aaaaaaaaaa aaa          1748

<210> SEQ ID NO 2
<211> LENGTH: 534
<212> TYPE: PRT
<213> ORGANISM: Zea mays L

<400> SEQUENCE: 2

Met Ala His Arg Gly His Leu Asp Gly Leu Thr Gly Gln Ala Pro Ala
1               5                   10                  15
```

-continued

```
Leu Met Arg His Gly Ser Phe Ala Ala Gly Ser Leu Ser Ser Arg Ser
             20                  25                  30

Pro Leu Gln Ser Ser Thr Leu Glu Met Leu Glu Asn Lys Leu Ala
         35                  40                  45

Met Gln Thr Thr Glu Val Glu Lys Leu Ile Thr Glu Asn Gln Arg Leu
     50                  55                  60

Ala Ser Ser His Val Val Leu Arg Gln Asp Ile Val Asp Thr Glu Lys
 65                  70                  75                  80

Glu Met Gln Met Ile Arg Thr His Leu Gly Glu Val Gln Thr Glu Thr
                 85                  90                  95

Asp Leu Gln Ile Arg Asp Leu Leu Glu Arg Ile Arg Leu Met Glu Val
            100                 105                 110

Asp Ile His Ser Gly Asn Val Val Asn Lys Glu Leu His Gln Met His
            115                 120                 125

Met Glu Ala Lys Arg Leu Ile Thr Glu Arg Gln Met Leu Thr Leu Glu
    130                 135                 140

Ile Glu Asp Val Thr Lys Glu Leu Gln Lys Leu Ser Ala Ser Gly Asp
145                 150                 155                 160

Asn Lys Ser Leu Pro Glu Leu Leu Ser Glu Leu Asp Arg Leu Arg Lys
                165                 170                 175

Glu His His Asn Leu Arg Ser Gln Phe Glu Phe Glu Lys Asn Thr Asn
            180                 185                 190

Val Lys Gln Val Glu Gln Met Arg Thr Met Glu Met Asn Leu Ile Thr
        195                 200                 205

Met Thr Lys Gln Ala Glu Lys Leu Arg Val Asp Val Ala Asn Ala Glu
    210                 215                 220

Arg Arg Ala Gln Ala Ala Ala Gln Ala Ala His Ala Ala Gly
225                 230                 235                 240

Ala Gln Val Thr Ala Ser Gln Pro Gly Gln Leu Lys Leu Pro Arg Phe
        245                 250                 255

Gln Gln Gln Gln Pro Gln Thr His Met Gln Val His Ile Pro Ala Thr
                260                 265                 270

Pro Leu His Ile Ser Arg Glu Pro Arg Leu Gly His Ile Ser Arg Val
            275                 280                 285

Leu Arg Leu Gly Tyr Ile Ser Arg Glu Pro Arg Leu Gly His Ile Ser
    290                 295                 300

Arg Glu Pro Arg Leu Gly His Ile Ser Arg Gly Ala Arg Met Gly His
305                 310                 315                 320

Ile Ser Arg Gly Leu Arg Leu Gly His Ile Ser Arg Glu Pro Arg Leu
                325                 330                 335

Gly His Ile Ser Arg Glu Pro Arg Leu Gly His Ile Ser Arg Val Leu
            340                 345                 350

Arg Leu Gly His Ile Ser Arg Glu Pro Arg Leu Gly His Ile Ser Arg
        355                 360                 365

Gly Pro Ser Leu Gly His Ile Ser Arg Gly Pro Arg Leu Gly His Ile
    370                 375                 380

Ser Arg Glu Pro Arg Met Gly His Ile Ser Arg Glu Pro Arg Met Gly
385                 390                 395                 400

His Ile Ser Arg Val Leu Arg Leu Glu His Thr Thr Met Leu Met Met
                405                 410                 415

Leu Ala Arg Leu Met His Met Gln Val Thr Leu Ala Ile Gln Leu Gln
            420                 425                 430

Ala Thr Arg Lys Val Gln Cys Pro Thr Ile Pro Met Leu His Leu Arg
```

```
                         435                 440                 445
Ser Gln Gln Ala Ala Val Gln Leu Arg Thr Pro Gln Glu Ala Ser Met
    450                 455                 460

Gly Gln Leu Val Val Leu Asp Ile Leu Leu Gly Lys Phe Ser Arg Ala
465                 470                 475                 480

Val Ala Leu Gln Met Gln Arg Lys His Leu Leu His His His Arg
                485                 490                 495

Gln His His Ile Pro Pro Ala His Met Thr Lys Pro Glu Glu Pro Arg
            500                 505                 510

Asp Lys Ile Trp Asp Val Asn Gln Met Asp Val Cys His Ala His Leu
        515                 520                 525

Leu Ser Arg Gln Ile Trp
    530

<210> SEQ ID NO 3
<211> LENGTH: 1910
<212> TYPE: DNA
<213> ORGANISM: Zea mays L
<220> FEATURE:
<221> NAME/KEY: repeat_region
<222> LOCATION: (823)..(1389)
<223> OTHER INFORMATION: rpt unit (823).. (849) number rpt: 21 repeats
<220> FEATURE:
<221> NAME/KEY: CDS
<222> LOCATION: (1)..(1764)
<223> OTHER INFORMATION: coding sequence
<220> FEATURE:
<221> NAME/KEY: polyA_site
<222> LOCATION: (1892)..(1910)
<223> OTHER INFORMATION: polyadenylation site
<220> FEATURE:
<221> NAME/KEY: 3'UTR
<222> LOCATION: (1765)..(1891)
<223> OTHER INFORMATION: 3'untranslated region

<400> SEQUENCE: 3 atg gct cat cgt gga cat cta gat gga ctg act ggc caa gct cct gct      48
Met Ala His Arg Gly His Leu Asp Gly Leu Thr Gly Gln Ala Pro Ala
1               5                   10                  15 ctt atg cgc cat ggt tcc ttc gct gca ggc agc ctc tct agc cgc tca      96
Leu Met Arg His Gly Ser Phe Ala Ala Gly Ser Leu Ser Ser Arg Ser
            20                  25                  30 cct ttg cag tct tca tcc aca ctg gag atg ctg gag aac aag ctt gcc     144
Pro Leu Gln Ser Ser Ser Thr Leu Glu Met Leu Glu Asn Lys Leu Ala
        35                  40                  45 atg caa act aca gaa gtg gaa aag ctt atc acg gag aat cag cgg tta     192
Met Gln Thr Thr Glu Val Glu Lys Leu Ile Thr Glu Asn Gln Arg Leu
    50                  55                  60 gca tca agc cat gtg gtc ttg agg cag gac att gtt gat acg gag aaa     240
Ala Ser Ser His Val Val Leu Arg Gln Asp Ile Val Asp Thr Glu Lys
65                  70                  75                  80 gag atg caa atg atc cgc acc cac cta ggt gaa gtt cag aca gag act     288
Glu Met Gln Met Ile Arg Thr His Leu Gly Glu Val Gln Thr Glu Thr
                85                  90                  95 gat ttg cag att aga gat ttg ttg gag aga atc aga tta atg gag gta     336
Asp Leu Gln Ile Arg Asp Leu Leu Glu Arg Ile Arg Leu Met Glu Val
            100                 105                 110 gat ata cat agt ggt aat gta gtg aac aag gag ctt cac caa atg cat     384
Asp Ile His Ser Gly Asn Val Val Asn Lys Glu Leu His Gln Met His
        115                 120                 125 atg gag gca aag aga ctt att act gaa agg cag atg cta acc ctt gag     432
Met Glu Ala Lys Arg Leu Ile Thr Glu Arg Gln Met Leu Thr Leu Glu
    130                 135                 140
```

-continued

```
ata gag gat gtg act aaa gaa tta cag aaa ctc tct gcc tct ggg gac    480
Ile Glu Asp Val Thr Lys Glu Leu Gln Lys Leu Ser Ala Ser Gly Asp
145                 150                 155                 160 aat aaa agc ctt cct gaa ttg ctt tct gag cta gat agg cta cgg aaa    528
Asn Lys Ser Leu Pro Glu Leu Leu Ser Glu Leu Asp Arg Leu Arg Lys
                165                 170                 175 gag cat cat aat tta cga tct cag ttt gaa ttt gag aaa aat aca aac    576
Glu His His Asn Leu Arg Ser Gln Phe Glu Phe Glu Lys Asn Thr Asn
            180                 185                 190 gtc aag caa gtt gag cag atg cgg aca atg gaa atg aac ttg ata acc    624
Val Lys Gln Val Glu Gln Met Arg Thr Met Glu Met Asn Leu Ile Thr
        195                 200                 205 atg acc aaa caa gct gag aag tta cgt gtt gat gtg gca aat gct gaa    672
Met Thr Lys Gln Ala Glu Lys Leu Arg Val Asp Val Ala Asn Ala Glu
    210                 215                 220 aga cgg gca caa gca gct gcg gct caa gca gca gca cat gca gct ggt    720
Arg Arg Ala Gln Ala Ala Ala Ala Gln Ala Ala Ala His Ala Ala Gly
225                 230                 235                 240 gca cag gtg aca gct tcg cag cct gga cag ctc aag cta cca cgg ttt    768
Ala Gln Val Thr Ala Ser Gln Pro Gly Gln Leu Lys Leu Pro Arg Phe
                245                 250                 255 cag cag cag cag cca cag act cat atg cag gtg cat ata cca gct acc    816
Gln Gln Gln Gln Pro Gln Thr His Met Gln Val His Ile Pro Ala Thr
                260                 265                 270 ccc ctg cat atc agc agg gag ccc agg ctg ggg cat atc agc agg gtg    864
Pro Leu His Ile Ser Arg Glu Pro Arg Leu Gly His Ile Ser Arg Val
            275                 280                 285 ctc agg ctg ggg tat atc agc agg gag ccc agg ctg ggg cat atc agc    912
Leu Arg Leu Gly Tyr Ile Ser Arg Glu Pro Arg Leu Gly His Ile Ser
        290                 295                 300 agg gag ccc agg ctg ggg cat atc agc agg ggg gcc agg atg ggg cat    960
Arg Glu Pro Arg Leu Gly His Ile Ser Arg Gly Ala Arg Met Gly His
305                 310                 315                 320 atc agc agg ggg ctc agg ctg ggg cat atc agc agg gag ccc agg ctg   1008
Ile Ser Arg Gly Leu Arg Leu Gly His Ile Ser Arg Glu Pro Arg Leu
                325                 330                 335 ggg cat atc agc agg gag ccc agg ctg ggg cat atc agc agg gtg ctc   1056
Gly His Ile Ser Arg Glu Pro Arg Leu Gly His Ile Ser Arg Val Leu
            340                 345                 350 agg ctg ggg cat atc agc agg gtg ctc agg ctg ggg tat atc agc agg   1104
Arg Leu Gly His Ile Ser Arg Val Leu Arg Leu Gly Tyr Ile Ser Arg
        355                 360                 365 gaa ccc agg ctg ggg cat atc agc agg gag ccc agg ctg ggg cat atc   1152
Glu Pro Arg Leu Gly His Ile Ser Arg Glu Pro Arg Leu Gly His Ile
370                 375                 380 agc agg ggg gcc agg atg ggg cat atc agc agg ggg ctc agg ctg ggg   1200
Ser Arg Gly Ala Arg Met Gly His Ile Ser Arg Gly Leu Arg Leu Gly
385                 390                 395                 400 cat atc agc agg gag ccc agg ctg ggg cat atc agc agg gag ccc agg   1248
His Ile Ser Arg Glu Pro Arg Leu Gly His Ile Ser Arg Glu Pro Arg
                405                 410                 415 ctg ggg cat atc agc agg ggg ccc agt ctg ggg cat atc agc agg ggg   1296
Leu Gly His Ile Ser Arg Gly Pro Ser Leu Gly His Ile Ser Arg Gly
            420                 425                 430 ccc agg ctg ggg cat atc agc agg gag ccc agg atg ggg cat atc agc   1344
Pro Arg Leu Gly His Ile Ser Arg Glu Pro Arg Met Gly His Ile Ser
        435                 440                 445 agg gag ccc agg atg ggg cat atc agc agg gtg ctc agg ctg gag cat   1392
Arg Glu Pro Arg Met Gly His Ile Ser Arg Val Leu Arg Leu Glu His
```

```
              450                 455                 460
aca act atg ctt atg atg ctg gca cgg ctt atg cat atg cag gtt act      1440
Thr Thr Met Leu Met Met Leu Ala Arg Leu Met His Met Gln Val Thr
465                 470                 475                 480 ctg gct atc cag ttg cag gct acg cgc aaa gtg cag tgc cca act att      1488
Leu Ala Ile Gln Leu Gln Ala Thr Arg Lys Val Gln Cys Pro Thr Ile
                    485                 490                 495 cct atg ctg cac ctc cgc agc caa caa gca gcg gtg cag cta cga acg      1536
Pro Met Leu His Leu Arg Ser Gln Gln Ala Ala Val Gln Leu Arg Thr
                500                 505                 510 ccg cag gag gcc agt atg ggg cag ttg gta gtg ctg gat atc cta ctg      1584
Pro Gln Glu Ala Ser Met Gly Gln Leu Val Val Leu Asp Ile Leu Leu
            515                 520                 525 ggc aag ttc agc cga gca gtg gca ctg caa atg cag cgc aag cac ctc      1632
Gly Lys Phe Ser Arg Ala Val Ala Leu Gln Met Gln Arg Lys His Leu
        530                 535                 540 ctc ctc cac cac cac cgg cag cac cat atc ccc cca gca cat atg acc      1680
Leu Leu His His His Arg Gln His His Ile Pro Pro Ala His Met Thr
545                 550                 555                 560 aaa cca gag gag ccc aga gat aaa atc tgg gat gta aac cag atg gat      1728
Lys Pro Glu Glu Pro Arg Asp Lys Ile Trp Asp Val Asn Gln Met Asp
                565                 570                 575 gtt tgc cat gca cat ttg ttg agc aga caa ata tgg tgaaatctgg           1774
Val Cys His Ala His Leu Leu Ser Arg Gln Ile Trp
                580                 585 gatgtaaaac cagatggctg tctgtgcctc catcccattg actagggcgt attttcacca    1834
atattgtgcc tccagtgcaa tttcttctgt gttatatatc accaccattt gttgggcaaa    1894
aaaaaaaaaa aaaaa                                                     1910

<210> SEQ ID NO 4
<211> LENGTH: 588
<212> TYPE: PRT
<213> ORGANISM: Zea mays L

<400> SEQUENCE: 4

Met Ala His Arg Gly His Leu Asp Gly Leu Thr Gly Gln Ala Pro Ala
1               5                   10                  15

Leu Met Arg His Gly Ser Phe Ala Ala Gly Ser Leu Ser Ser Arg Ser
                20                  25                  30

Pro Leu Gln Ser Ser Ser Thr Leu Glu Met Leu Glu Asn Lys Leu Ala
            35                  40                  45

Met Gln Thr Thr Glu Val Glu Lys Leu Ile Thr Glu Asn Gln Arg Leu
        50                  55                  60

Ala Ser Ser His Val Val Leu Arg Gln Asp Ile Val Asp Thr Glu Lys
65                  70                  75                  80

Glu Met Gln Met Ile Arg Thr His Leu Gly Glu Val Gln Thr Glu Thr
                85                  90                  95

Asp Leu Gln Ile Arg Asp Leu Leu Glu Arg Ile Arg Leu Met Glu Val
            100                 105                 110

Asp Ile His Ser Gly Asn Val Val Asn Lys Glu Leu His Gln Met His
        115                 120                 125

Met Glu Ala Lys Arg Leu Ile Thr Glu Arg Gln Met Leu Thr Leu Glu
    130                 135                 140

Ile Glu Asp Val Thr Lys Glu Leu Gln Lys Leu Ser Ala Ser Gly Asp
145                 150                 155                 160

Asn Lys Ser Leu Pro Glu Leu Leu Ser Glu Leu Asp Arg Leu Arg Lys
```

```
                165                 170                 175
Glu His His Asn Leu Arg Ser Gln Phe Glu Phe Glu Lys Asn Thr Asn
            180                 185                 190
Val Lys Gln Val Glu Gln Met Arg Thr Met Glu Met Asn Leu Ile Thr
            195                 200                 205
Met Thr Lys Gln Ala Glu Lys Leu Arg Val Asp Val Ala Asn Ala Glu
            210                 215                 220
Arg Arg Ala Gln Ala Ala Ala Gln Ala Ala His Ala Ala Gly
225                 230                 235                 240
Ala Gln Val Thr Ala Ser Gln Pro Gly Gln Leu Lys Leu Pro Arg Phe
            245                 250                 255
Gln Gln Gln Gln Pro Gln Thr His Met Gln Val His Ile Pro Ala Thr
            260                 265                 270
Pro Leu His Ile Ser Arg Glu Pro Arg Leu Gly His Ile Ser Arg Val
            275                 280                 285
Leu Arg Leu Gly Tyr Ile Ser Arg Glu Pro Arg Leu Gly His Ile Ser
            290                 295                 300
Arg Glu Pro Arg Leu Gly His Ile Ser Arg Gly Ala Arg Met Gly His
305                 310                 315                 320
Ile Ser Arg Gly Leu Arg Leu Gly His Ile Ser Arg Glu Pro Arg Leu
            325                 330                 335
Gly His Ile Ser Arg Glu Pro Arg Leu Gly His Ile Ser Arg Val Leu
            340                 345                 350
Arg Leu Gly His Ile Ser Arg Val Leu Arg Leu Gly Tyr Ile Ser Arg
            355                 360                 365
Glu Pro Arg Leu Gly His Ile Ser Arg Glu Pro Arg Leu Gly His Ile
            370                 375                 380
Ser Arg Gly Ala Arg Met Gly His Ile Ser Arg Gly Leu Arg Leu Gly
385                 390                 395                 400
His Ile Ser Arg Glu Pro Arg Leu Gly His Ile Ser Arg Glu Pro Arg
            405                 410                 415
Leu Gly His Ile Ser Arg Gly Pro Ser Leu Gly His Ile Ser Arg Gly
            420                 425                 430
Pro Arg Leu Gly His Ile Ser Arg Glu Pro Arg Met Gly His Ile Ser
            435                 440                 445
Arg Glu Pro Arg Met Gly His Ile Ser Arg Val Leu Arg Leu Glu His
            450                 455                 460
Thr Thr Met Leu Met Met Leu Ala Arg Leu Met His Met Gln Val Thr
465                 470                 475                 480
Leu Ala Ile Gln Leu Gln Ala Thr Arg Lys Val Gln Cys Pro Thr Ile
            485                 490                 495
Pro Met Leu His Leu Arg Ser Gln Gln Ala Ala Val Gln Leu Arg Thr
            500                 505                 510
Pro Gln Glu Ala Ser Met Gly Gln Leu Val Val Leu Asp Ile Leu Leu
            515                 520                 525
Gly Lys Phe Ser Arg Ala Val Ala Leu Gln Met Gln Arg Lys His Leu
            530                 535                 540
Leu Leu His His Arg Gln His His Ile Pro Pro Ala His Met Thr
545                 550                 555                 560
Lys Pro Glu Glu Pro Arg Asp Lys Ile Trp Asp Val Asn Gln Met Asp
            565                 570                 575
Val Cys His Ala His Leu Leu Ser Arg Gln Ile Trp
            580                 585
```

```
<210> SEQ ID NO 5
<211> LENGTH: 16
<212> TYPE: DNA
<213> ORGANISM: Artificial sequence
<220> FEATURE:
<223> OTHER INFORMATION: Oligonucleotide E1

<400> SEQUENCE: 5
gattctccct gataag                                                    16

<210> SEQ ID NO 6
<211> LENGTH: 36
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (24)..(25); (29)..(30); (34)..(35)
<223> OTHER INFORMATION: n= inosine: a rare base that is important at
      the wobble (3rd) position of some tRNA anticodons" used by the
      commercial primer 5' RACE Abridged Anchor Primer (GIBCO BRL r)
      that corresponds to SEQ ID No 6

<400> SEQUENCE: 6
ggccaggcgt cgactagtac gggnngggnn gggnng                              36

<210> SEQ ID NO 7
<211> LENGTH: 18
<212> TYPE: DNA
<213> ORGANISM: Artificial sequence
<220> FEATURE:
<223> OTHER INFORMATION: Oligonucleotide E2

<400> SEQUENCE: 7
gttctccagc atctccag                                                  18
```